United States Patent
Olvera et al.

(10) Patent No.: US 7,435,846 B2
(45) Date of Patent: Oct. 14, 2008

(54) ABSORPTION AND BIOAVAILABILITY OF CAROTENOIDS, FORMULATIONS AND APPLICATIONS

(75) Inventors: Ricardo Montoya Olvera, Monterrey (MX); José Torres Quiroga, Garza Garcia (MX)

(73) Assignee: Industrial Organica, S.A. De C.V., Monterrey, N.L. (MX)

( * ) Notice: Subject to any disclaimer, the term of this patent is extended or adjusted under 35 U.S.C. 154(b) by 110 days.

(21) Appl. No.: 11/506,974

(22) Filed: Aug. 18, 2006

(65) Prior Publication Data

US 2008/0044475 A1  Feb. 21, 2008

(51) Int. Cl.
*C07C 69/00* (2006.01)
*C07C 69/02* (2006.01)

(52) U.S. Cl. ...................... 560/231; 560/130
(58) Field of Classification Search ........................ None
See application file for complete search history.

(56) References Cited

U.S. PATENT DOCUMENTS

| | | | |
|---|---|---|---|
| 2,861,891 A | 11/1958 | Bauernfeind | |
| 3,523,138 A | 8/1970 | Grant | |
| 3,535,426 A | 10/1970 | Hawks | |
| 5,364,563 A | 11/1994 | Cathrein | |
| 5,496,813 A | 3/1996 | Eugster | |
| 5,536,504 A | 7/1996 | Eugster | |
| 5,827,539 A | 10/1998 | Gellenbeck | |
| 5,863,953 A | 1/1999 | Luddecke et al. | |
| 5,891,907 A | 4/1999 | Kolter et al. | |
| 5,895,659 A | 4/1999 | Luddecke et al. | |
| 5,925,684 A | 7/1999 | Schweikert et al. | |
| 5,968,251 A | 10/1999 | Auweter et al. | |
| 5,976,575 A | 11/1999 | Gellenbeck | |
| 6,075,058 A | 6/2000 | Handelman | |
| 6,093,348 A | 7/2000 | Kowalski et al. | |
| 6,132,790 A | 10/2000 | Schliapalius | |
| 6,180,130 B1 * | 1/2001 | Chen et al. | 424/439 |
| 6,261,622 B1 | 7/2001 | Koguchi et al. | |
| 6,328,995 B1 | 12/2001 | Bewert et al. | |
| 6,406,735 B2 | 6/2002 | Stein et al. | |
| 6,936,279 B2 | 8/2005 | Guerra-Santos et al. | |
| 2004/0170734 A1 * | 9/2004 | Fujii et al. | 426/540 |

FOREIGN PATENT DOCUMENTS

WO  WO 9947001  9/1999

* cited by examiner

*Primary Examiner*—Karl J Puttlitz
(74) *Attorney, Agent, or Firm*—Abelman, Frayne & Schwab

(57) ABSTRACT

A process for obtaining a microscopic physical state of xanthophylls or oxycarotenoids derivatives forms such as diacetates or dipropionates derivatives, which are readily incorporated in the digestive system as micelles providing an improved bioavailability, as compared to the bioavailability of carotenoids that are ingested in diverse preparations that contain microscopic carotenoids crystals and a method for its application.

16 Claims, No Drawings

ABSORPTION AND BIOAVAILABILITY OF CAROTENOIDS, FORMULATIONS AND APPLICATIONS

BACKGROUND OF THE INVENTION

A. Field of the Invention

The present invention is related to a process that noticeably improves the bioavailability of carotenoids by obtaining carotenoid micelles in a lipid matrix in the presence of water. Such lipid matrix is composed of the free fatty acids to which the xanthophylls are naturally bound, and the waxes, phospholipids and sterols that naturally occur in the carotenoids' extracts, as well as emulsifying agents. During the esterification reaction of lutein, zeaxanthin, and other carotenoids with short chain organic acids, such as acetic or propionic acids, and further processing, the formation of carotenoid micelles occur in a lipid matrix that have been found to be readily absorbed through the intestinal wall. Such absorption is a noticeable improvement as compared to the lower bioavailability of carotenoid crystals. The invention also relates to formulations of carotenoid microemulsions and nanoemulsions that improve the bioavailability in humans, poultry and marine organisms.

B. Description of the Related Art

Carotenoids are terpenoid compounds that besides their typical pigmenting characteristics (yellow, orange or red pigments), function as precursors of molecules with biological activity intervening in different vital biological and physiological processes.

Over 600 different carotenoids have been recognized in nature. Carotenoids are classified in two major groups: carotenes, which are hydrocarbon molecules comprising atoms of carbon and hydrogen only. Representative examples of carotenes include β-Carotene and Lycopene. And xanthophylls, which are oxygenated derivatives of the carotenes. Examples of xanthophylls include Lutein, Zeaxanthin, Isozeaxanthin, Capsanthin, Capsorubin, Cryptoxanthin, Astaxanthin, 3' Epilutein, and Cantaxanthin.

Carotenoids are widely distributed in nature. Total annual production in nature is estimated at over 100 million tons. Carotenoids intervene in the physiology of all living organisms. They are produced in nature by photosynthetic and enzymatic reactions carried by marine microorganisms as microalgae, bacteria, fungii and zooplancton; and in most terrestrial living plants occur in their leaves, flowers and fruits.

In flowers and fruits, carotenoids impart vivid yellow, orange and red colors.

In birds, carotenoids play the role of vital functions as well as cosmetic purposes, they differentiate genders, and are indicative of sexual maturity and attraction.

In marine organisms, carotenoids are more abundant than in terrestrial organisms and they are responsible for several vital biological, physiological, metabolic and reproductive functions. Carotenoids provide color to marine microalgae and bacteria, krill, salmon, trout, red sea bream, yellow tail tuna, crustaceans, etc.

No animal species are capable of synthesizing carotenoids. Therefore, they must obtain their requirements through their diet. Broilers and layers grown in captivity require a given dose of lutein and zeaxanthin in their feed in order to supplement their requirements. Laying hens accumulate lutein, zeaxanthin and cantaxanthin in the yolk, protecting the embryo against the oxidative damage provoked by the free radicals that occur due to the high rate of metabolic reactions in the rapidly developing embryo. Broilers, on the other hand, accumulate lutein and zeaxanthin in their adipose tissue as well as in the skin. Such deposits act as reservoirs of carotenoids, and become available when required to perform specific physiological functions.

Some carotenoids are metabolized by terrestrial or marine organisms into Vitamin A, and such carotenoids are the only source of Vitamin A for herbivores or omnivores living in their natural environment.

Carotenoids act as effective antioxidants in most living organisms. They have the capability to quench free radicals that are produced in metabolic reactions at the cellular level, avoiding tissue degradation.

Extensive research in the past years indicate that the presence of lutein and zeaxanthin in the macula helps the prevention of age related macular degeneration in humans, as well as avoiding the development of cataracts. Lutein and zeaxanthin are also present in human breast milk, and in the adipose tissues.

Dark green leafy vegetables, tomatoes, as well as yellow corn, and many fruits like oranges, mangoes, grapefruit, etc. are the natural source of dietary carotenoids. Carotenoids occur in a concentrated way in chromoplasts attached to proteins or fibers by non-covalent links. However, chloroplast or chromoplast and other plant structural materials may not be the ideal source of carotenoids for human consumption due to their low bioavailability. Carotenoids occur in food plants as part of the photosynthetic apparatus (green leafy vegetables), dissolved in oil droplets (fruits) or as semi crystalline membrane-bound solids (carrot, tomato). Fatty acid esters of carotenoids, such as lutein, zeaxanthin and cryptoxanthin, occur in some fruits (peaches, papaya, peppers), as well as in xanthophyll concentrates obtained from marigold (*Tagetes erecta*) and red peppers (*Capsicum annum*).

To insure that the carotenoids are absorbed by the organism, they should first be freed from their chromoplast matrix. They are thought to be hydrolyzed in the intestinal lumen before mucosal uptake, most likely by the carboxylic ester hydrolase secreted by the pancreas.

In animals, the absorption of carotenoids is generally accepted as following the absorption of lipids—i.e. emulsification and incorporation into mixed micelles, which are then absorbed by the mucosa of the small intestine, mainly in the duodenum, in parallel with fat digestion and absorption. They are transported through the unstirred water layer and taken up by the enterocytes by passive diffusion.

It is in the intestinal mucous wall that such passive diffusion is improved if the carotenoids are dissolved in a lipid forming a micelle in an aqueous media, rather than if they are in crystalline form. Crystals are not the ideal physical form for this diffusion to occur, nor are carotenoids crystals readily incorporated into micelles. If the carotenoids enter the gut already in the form of microemulsions, or as nanoemulsions, the formation of micelles is facilitated.

After the carotenoids are absorbed, they are transported through the enterocytes from the luminal side to the serosal side. They are packaged in chylomicrons and secreted into the thoracic duct, and find their way into the circulating blood via the vena cava inferior.

Among the main factors that affect the bioavailability of xanthophylls by organisms are: physical form in the source (food matrix), the structure of the xanthophylls molecules, and the interaction of the xanthophylls with other nutrients, mainly lipids. Therefore, it would be highly desirable to develop carotenoid compounds, derivatives or formulations with improved stability, absorption and bioavailability.

Many natural and processed foods consist either partly or wholly as emulsions or have been in an emulsified state at some time during their production. The manufacture of an emulsion-based food product with quality attributes depends on the selection of the most appropriate raw materials (e.g., water, oil, emulsifier, thickening agents, minerals, acids, colorants, flavours, vitamins, etc.) and processing conditions (e.g.—mixing, homogenization, pasteurizations, sterilization, etc.).

An emulsion is a mixture of two immiscible liquids (usually oil and water), with one of them dispersed as small spherical droplets in the other phase. Emulsions can be conveniently classified according to the distribution of the oil and aqueous phases. A system which consist of oil droplets dispersed in an aqueous phase is called an oil-in-water or O/W emulsion (e.g., mayonnaise, milk, cream, soups and sauces). A system which consists of water droplets dispersed in an oil phase is called a water-in oil or W/O (e.g., margarine, butter and spreads). Emulsions are part of a more general class of two-phase systems of matter called colloids. Although the terms colloid and emulsion are sometimes used interchangeably, emulsion tends to imply that both the dispersed and the continuous phase are liquid. An emulsifier (also known as a surfactant from surface active material or emulgent) is a substance which stabilizes an emulsion.

The main role of the surfactants in food emulsions is to enhance their formation and stability. Surfactants used in the food industry are mainly nonionic (e.g., monoacylglycerols, sucrose esters of fatty acids), anionic (e.g., fatty acids), or zwitterionic (e.g., lecithin). Surfactants aggregate spontaneously in solution to form a variety of thermodynamically stable structures know as association colloids (e.g., micelles, bilayers, vesicles, and reverse micelles). The shape of a micelle is controlled largely by the molecular geometry of its surfactant molecules, but micelle shape also depends on the conditions, such as temperature or pH, and the type and concentration of any added salt.

Nonpolar molecules, which are normally insoluble or only sparingly soluble in water, can be solubilized in an aqueous surfactant solution by incorporation into micelles or other types of association colloids. Micelles containing solubilizied materials are referred to as microemulsions or swollen micelles, whereas the materials solubilizied within the micelle are referred to as the solubilizate.

In view of the above referred needs, applicants developed a process for obtaining a microscopic physical state of xanthophylls or oxycarotenoids derivatives forms, such as diacetates and dipropionates derivatives, that are readily incorporated in the digestive system as micelles providing an improved bioavailabilty, as compared to the bioavailability of carotenoids that are ingested in crystalline form.

U.S. Pat. No. 2,861,891 issued to Bauernfeind and Howard describes a process to obtain a dry powder, obtaining a supersaturated carotene solution by heating in a vegetable oil that afterwards is dispersed in an aqueous gelable colloid solution, and converting the emulsion thus formed into a dry particulate form. Such process involves heating the carotenoids in vegetable oil in order to improve the solubility of the carotenes, lycopene, lutein, zeaxanthin, cryptoxanthin, bixin and methyl bixin, and avoiding the precipitation of carotenoids crystals by incorporating a gelable colloid. A further emulsification step follows in an aqueous colloidal solution that forms a gel capable of producing a dry powder after a spray drying process. The product obtained is a microcrystalline dispersion in edible oil used to impart color to margarine, fruits and vegetables in which the βcarotene occurs in the form of microdispersion in a protective hydrophilic colloid.

U.S. Pat. No. 3,523,138 issued to Grant describes the improved bioavailability of carotenoids in poultry, after a saponification reaction has taken place in order to free the xanthophylls from the long chain fatty acid esters.

U.S. Pat. No. 3,535,426 issued to Hawks discloses that a saponified mixture of xanthophylls become more stable, and consequently more bioavailable, when admixed with a fat and ethoxyquinolein.

Cathrein describes in U.S. Pat. No. 5,364,563 a process for producing powdered carotenoid preparations by obtaining a suspension in oil that is brought in contact with superheated steam, producing an emulsion that is spray dried.

Eugster et al, in U.S. Pat. Nos. 5,496,813 and 5,536,504 obtain ultra microemulsions that form spontaneously dispersible concentrates containing xanthophylls esters that have anti tumor activity.

Gellenbeck in U.S. Pat. No. 5,827,539 obtains a finely ground mixture of carotenoids with an oil and a spray dried encapsulated form that is water dispersible.

Luddecke, et al, in U.S. Pat. No. 5,863,953 describes the obtention of an oil dispersion of carotenoids, which is used to prepare a double dispersion system with particles sizes of 100 microns, stabilized by a protective colloid and emulsifiers.

Sanders and Herink published in WO9947001 the increased bioavailability of lutein and zeaxanthin in humans and poultry using isolecithin and lecithin.

Kolter et al, describe in U.S. Pat. No. 5,891,907 stable aqueous solubilizates of carotenoids and vitamins, in which the carotenoids and the water insoluble vitamins with the aid of a nonionic emulsifier, yield a micelle, which particles are smaller than 100 nm.

Luddecke et al, describe in U.S. Pat. No. 5,895,659 the preparation of finely dispersed carotenoids or retinoid suspensions by dissolving the carotenoid or retinoid in a volatile, water-miscible organic solvent, under elevated pressures, and immediately after 10 seconds, mix the solution with an aqueous medium containing an emulsifier.

Schweikert et al in U.S. Pat. No. 5,925,684 describe a stable oil in water emulsion consisting of an aqueous phase and an oil phase which is very finely dispersed by means of an emulsifier, and wherein the carotenoid is present in the oil phase in a concentration above the saturation solubility of the carotenoid in the oil at room temperature.

Auweter et al, describe in U.S. Pat. No. 5,968,251 the preparation of coldwater dispersible powders by preparing a molecular-disperse solution of a carotenoid, with or without an emulsifier and/or edible oil, in a volatile, water-miscible organic solvent at elevated temperature and adding an aqueous solution of a protective colloid; whereupon the hydrophilic solvent is transferred into the aqueous phase, and the hydrophobic phase of the carotenoid results as a nanodisperse phase, removing the solvent by heating the hydrosol and converting it in a water dispersible dry powder.

Gellenbeck in U.S. Pat. No. 5,976,575 describes the grinding of a mixture of carotenoids and oil to reduce the carotenoids particle size, emulsifying the mixture with an encapsulating mixture and drying the emulsion.

Handelman in U.S. Pat. No. 6,075,058 describes the composition of lutein and zeaxanthin along with cholesterol, olive oil, egg yolk phospholipids, alpha tocopherol and aqueous sodium chloride. The mixture is prepared by mixing the lipid ingredients into ethanol, evaporating the ethanol, and dispersing the lipids as an emulsion in the sodium chloride solution.

Kowalski et al, describe in U.S. Pat. No. 6,093,348 a method for the manufacture of carotenoid powders, weherein an aqueous suspension of the carotenoid is heated to melt the cardtenoid in the presence of a surfactant and a protective colloid under high temperatures and high pressures (HTHP process). The suspension is then homogenized under high pressure to form an emulsion. And the resulting emulsion is dried to obtain the carotenoid powder.

Schliapalius in U.S. Pat. No. 6,132,790 describes a composition of a carotenoid in oil, a dispersion of a water dispersible matrix and a stabilizer, and a non-oil solvent and an emulsifier, all of natural sources.

Koguchi, et al describe in U.S. Pat. No. 6,261,622 a method to provide a water-dispersible carotenoid preparation which can be added to various aqueous compositions with retaining dispersion stability even at low temperature, by dispersing pulverized carotenoids crystals with soybean extract fibers as emulsion stabilizer.

Bewert et al, in U.S. Pat. No. 6,328,995 describe a procedure to stabilize dry powders which are insoluble in hot water and which contain one or more lipid soluble vitamins or carotenoids, formed in an aqueous dispersion containing a protein, a sugar and potassium and/or sodium phosphates.

Stein et al, describe in U.S. Pat. No. 6,406,735 a process for the preparation of a pulverous composition of a finely divided carotenoid or retinoid comprising; forming a suspension of the active ingredient in a water-immiscible organic solvent containing an antioxidant and/or an oil, feeding the suspension through a heat exchanger and heating the suspension to a high temperature for a 5 seconds residence time, rapidly mixing the solution with an aqueous swellable colloid and further removing the organic solvent to obtain the pulverous preparation, all steps processed in a continuous sequence.

Guerra-Santos, et al describe in U.S. Pat. No. 6,936,279 the obtention of microcrystalline form of carotenoids, particularly zeaxanthin, in an oily carrier. The "coarse-grained" carotenoids is dissolved in a suitable solvent as tetrahydrofuran, and mixed with a vegetable oil and an emulsifier. The mixture is injected along with an inert gas into a vacuum chamber in order to remove the solvent in a flash manner, not allowing the carotenoids crystals to grow. They obtain a microcrystalline suspension in the oil carrier.

All of the above references are related to carotenes, carotenoids or oxycarotenoids in their free and pure form and in no instance refer to carotenoids or oxycarotenoids derivatives, such as diacetates, or dipropionates or to any carotenoids or oxycarotenoid compound or derivative alone or as a complex.

Therefore, to the best of our knowledge, the process and formulation disclosed herein has not been disclosed in the prior art. Furthermore, none of the above described patents completely avoids the formation of carotenoids crystals, which as previously described, affect the absorption and bioavailability of carotenoids.

By the process of the present invention, it is possible to obtain microemulsions or nanoemulsions of lutein, 3'epilutein, and zeaxanthin diacetates and dipropionates, as well as short chain diesters of capsanthin, capsorubin, astaxantin and the acetate and propionate of cryptoxanthin that readily form micelles that are absorbed in the gut and diffuse through the mucous intestine wall.

Crystalline solids are composed of atoms, ions, or molecules in a highly ordered geometric pattern referred to as the crystal lattice. The atoms, ions or molecules are held in their positions by electrostatic, dipole and/or London forces. When a pure crystalline solid is heated, the atoms, ions or molecules vibrate more and more rapidly until at a definite temperature the thermal motion of the particles becomes great enough to overcome the forces of attraction. Then the atoms, ions or molecules enter a more random and mobile state, the liquid state. The melting point of a solid is defined as the temperature at which the liquid and solid phases are in equilibrium. A pure solid will generally melt sharply because the forces of attraction between the particles are the same. However, the presence of a foreign particle in a crystal lattice interrupts its uniform structure and the forces of attraction are weakened. An "impure" compound melts at a lower temperature and over a wider range. Thus, in the process of the present invention, the melting point of carotenoid derivatives is lowered (depressed) by the addition of a soluble material to the solution.

It is a common practice in the pigment industry to carry on a saponification reaction, or hydrolysis, of the fatty acids diesters of lutein and zeaxanthin as they naturally occur in the oleoresin of *Tagetes erecta*, in order to free the above mentioned carotenoids. It is also a common practice to hydrolyze the oleoresin of *Capsicum annum* to free the capsanthin and capsorubin from the fatty acids, as they occur in their natural form.

Such hydrolysis is carried out either in an aqueous media by means of a strong alkali and suitable emulsifiers and temperature, or in a non-polar organic media, such as propylene glycol, also under the action of a strong alkali and temperature. In both cases, as the xanthophylls are free they become insoluble in the reaction media and occur in crystalline form.

The reaction mass can be used to prepare pigment premixes or water dispersions, but the physical structure of the carotenoids is always microscopic crystals.

In the different purification and refinement processes aimed to obtain carotenoids of high purity, the saponified oleoresin mass is subject to several stages of selective organic polar, or non-polar, solvent extractions, or supercritical $CO_2$ extractions and recrystallizations in order to isolate the carotenoids from the other components of the mass. At the end of such purification processes, the carotenoids, as expected, occur in crystalline form.

In the process of the present invention the micelles, microemulsions and nanoemulsions of oxycarotenoid derivatives are obtained during the reaction of such oxycarotenoids with short chain organic acids, such as acetic or propionic acid. Such microscopic emulsions occur during the course of such reaction under controlled conditions and further processing. The carotenoid derivatives obtained by this process have melting points that are lower as compared to the melting points of the free carotenoids. Surprisingly, the carotenoid derivatives crystals under certain conditions of temperature, time, and in the presence of lipids, emulsifiers, and moisture, form stable micelles occluded in the lipid matrix and remain as such at normal conditions of temperature and pressure. Such lipid carotenoid micelles contain melt down oxycarotenoid derivatives, and are non-crystalline.

Furthermore, the present invention is related to a method for improving the absorption and bioavailability of carotenoids by humans and animals by providing a microscopic physical state of xanthophylls or oxycarotenoids derivative forms that are readily incorporated in the digestive system as micelles in the diet of humans and animals.

SUMMARY OF THE INVENTION

It is therefore a main object of the present invention, to provide a process for obtaining a microscopic physical state of xanthophylls or oxycarotenoid derivatives forms, such as diacetates or dipropionates derivatives, which are readily incorporated in the digestive system as micelles providing an improved bioavailability, as compared to the bioavailability of carotenoids that are ingested in diverse preparations that contain microscopic carotenoids crystals.

It is another object of the present invention to provide microemulsions or nanoemulsions of lutein, 3'epilutein and zeaxanthin diacetates and dipropionates, as well as short chain diesters of capsanthin, capsorubin, astaxanthin and the acetate and propionate of cryptoxanthin that readily form micelles according to the present invention that have an improved absorption and bioavailability.

This invention comprises and is related to the microscopic physical state of the xanthophylls or carotenoid derivatives, as well as the media in which they are incorporated into foods, supplements, beverages, or feeds. The invention comprises as well the improved bioavailability obtained with such physical form of the oxycarotenoids short chain diesters, such as diacetates and dipropionates derivatives.

The invention also relates to a process for the preparation of microemulsions and micelles and its uses in administering lutein and zeaxanthin diacetates or dipropionates, and those of other oxycarotenoids derivatives to humans, as well as for the pigmentation of broilers, egg yolks, and marine species as salmonids, crustaceans and fish.

It is still another object of the present invention to provide compounds which are derivatives of carotenoid having melting points that are lower as compared to the melting points of the free and pure carotenoids.

These and other objects and advantages of the present invention will become apparent to those persons having ordinary skill in the art, from the following detailed description of the embodiments of the invention.

DETAILED DESCRIPTION OF THE INVENTION

The process of the present invention will now be described making reference to a preferred embodiment thereof and to specific examples of use and application of the product, wherein the process of the present invention comprises:

(a) incorporating derivatives of oxycarotenoids selected from the group consisting of diacetates and dipropionates of lutein, 3'epilutein, zeaxanthin, mesozeaxanthin, capsanthin, and astaxanthin, and the monoacetate, of cryptoxanthin, monopropionate, and mixtures thereof, with the components of a vegetable matrix, or components of a similar nature, comprising fatty acids, phospholipids, emulsifiers, sterols or mixtures thereof inside a reactor;

(b) raising the temperature of the reactor to a temperature of about 60° to about 70° C. under a nitrogen atmosphere; (c) adding one or more surfactants in an amount of 5 to 50% by weight to the reactor mix, such as Tween 80, comprising polyoxyethylene sorbitan, particularly polysorbate 20-85 such as polysorbate 20, polysorbate 40, polysorbate 60, polysorbate 65, polysorbate 70, polysorbate 80(Tween 80), polysorbate 81, polysorbate 85; polyoxyethylene stearates (polyoxyethylene (40) stearate), polyoxyethylene (8) stearate and polyoxyethylene (40) stearate; polyoxyethylene oleates; polyoxyethylene laurates; polyoxyethylene castor oil derivatives; sorbitan esters; polyoxyethylene sorbitan fatty acid esters; poloxamers such as Pluronic F-65LF™.; Pluronic L-62LF™ and Pluronic L62D™ (BASF Wyandotte Corp.) or tyloxapol, polyoxyethylene fatty acid esters such as EMULPHOR™ (GAF Corp).

(d) stirring the mixture obtained in step c) for a period of time sufficient to homogenize the mixture (a typical period would be about two (2) hours);

(e) adding to the mixture obtained in step d) about 5 to about 50% of a phospholipids, by weight, said phospholipid selected from the group comprising: lecithins, phosphatidylcholine, phosphatidylethanolamine, or a purified phospholipid mixture, such as that obtained from egg yolk, or Lipoid E-80™ (Lipoid AG, which is a phospholipid mixture comprising about 50% phosphatidylcholine, 5% phosphatidylethanolamine, 3.6% non-polar lipids and about 2% sphingomyeline);

f) stirring the mixture obtained in step e) for a period of time sufficient to homogenize the mixture (a typical period would be about one (1) hour; g) adding to the mixture obtained in step f) of about 1 to about 40%, by weight, of water; and h) raising the temperature of the mixture obtained in step g) to about 90° to about 110° C. while maintaining the pH of the lipid matrix at from about 5.5 to about 8.5, preferably at a pH of from 6.5 to 7.0, and refluxing the mixture for a period of time sufficient to melt the crystals of carotenoid derivatives as observed under a 100× microscope in the lipid non-polar matrix, thus producing microemulsions of oxycarotenoid derivatives in a ratio of 0.001% to 40%, by weight, wherein the microemulsions comprise an internal homogeneous dispersed lipophilic phase of melted oxycarotenoids derivatives, and an external hydrophilic phase mainly formed by vegetable lipids and emulsifiers.

The microemulsions obtained can be reduced in size to obtain nanoemulsions by subjecting them to intense high speed and high shear mechanical agitators for a period of about 3 to about 4 hours, or by emulsifying machines operating at pressures on the order of about 3,000 to about 4,000 psi.

The microemulsions obtained in step h) may be dispersed in an aqueous or lipid media, suitable to be incorporated in human supplements or foods, or feeds for pets, poultry or aquatic animals at a temperature of between about 40° C. to 70° C. in order to, among other application, noticeably improve the absorption and bioavailability of xanthophylls diacetates and dipropionates obtained from lutein, zeaxanthin, capsanthin and capsorubin, for the purpose of pigmentation of broilers skin and egg yolks, or improving the bioavailability of the carotenoid derivatives obtained from lutein, zeaxanthin, capsanthin, capsorubin, and astaxanthin when incorporated in the feed of marine organisms, such as shrimp and crustaceans, salmon, trout, red sea bream, and yellow tail tuna.

The aqueous or lipid media microemulsions dispersion may comprise water containing derivatives of carotenoids obtained from lutein, 3'epilutein, zeaxanthin, isozeaxanthin, mesozeaxanthin, capsanthin, capsorubin, astaxanthin and cryptoxanthin, which can be administered to humans as a supplement to prevent the degeneration of human tissues due to the presence of free radicals; or oil-containing derivatives, preferably fish oil with a high content of omega 3 fatty acids, containing derivatives of carotenoids which noticeably improve the bioavailability of oxycarotenoid derivatives such as lutein, 3'epilutein, zeaxanthin, meso zeaxanthin, iso zeaxanthin, capsanthin, capsorubin and astaxanthin diacetates or dipropionates in humans which can be administered to humans as a supplement to prevent and protect cells and tissues from the damaging effects of free radicals and singlet oxygen, to improve the heart and cardiovascular conditions, and at the same time to help reduce the risk of macular degeneration and the formation of cataracts.

The microemulsion of carotenoids' derivatives obtained from lutein, 3'epilutein, zeaxanthin, iso-zeaxanthin, mesozeaxanthin, capsanthin, capsorubin, and astaxanthin obtained in step h) may also be encapsulated by suitable maltodextrins; sugars; animal, vegetable or fish gelatins in order to prepare beadlets for supplementing the nutrition of humans.

The above-described process helps the dissolution of crystals and avoids the recrystallization at room temperature of derivatives of oxycarotenoids contained in the original matrix.

Most of the carotenoids are unstable and tend to degrade when exposed to light, oxygen and organic or inorganic acids at elevated temperatures. While processing carotenoids under such conditions, all operations should be performed either under vacuum or under an inert atmosphere, such as a nitrogen atmosphere. It was observed that the short chain diester oxycarotenoids, namely diacetates or dipropionates displayed remarkable stability after being subjected to such conditions.

Since the diacetate and the dipropionates are derivatives of carotenoids of a non-polar nature, they tend to melt down and remain as micro or nanospheres dispersed in the lipid matrix at a temperature which is lower than the melting point of the pure carotenoids. The presence of lipids, free fatty acids, waxes and sterols, as they occur in natural oleoresin, called lipid matrix, also help to reduce the melting point of the oxycarotenoids derivatives.

It was found that after the hydrolysis of xanthophylls fatty acid esters is completed, and the excess alkali has been neutralized by means of a diluted acid like phosphoric acid, acetic acid, hydrochloric acid, perchloric acid, or mixtures thereof, and brought to a pH from about 5 to about 9, preferably a pH of about 5.5-6.5, a two phase system is formed. The organic phase that contains the carotenoids crystals is rinsed several times with warm water to remove any acid and traces of salts. The supernatant or lipid mass mainly consists of free fatty acids, and minor compounds like waxes, phospholipids and sterols, that occur naturally with the carotenoids esters. When this lipid mass is dried under vacuum and the carotenoids are esterified according to U.S. Pat. No. 5,959,138 with acetic anhydride or propionic anhydride, a supernatant organic phase is obtained where the carotenoids short chain diesters crystals are embedded. The compounds present in the organic matrix "impurities" interact by remarkably decreasing the carotenoids short chain diesters' melting point, and help to improve the stability of the oxycarotenoids derivatives during the heating process. The main fatty acids are myristic, palmitic and stearic as naturally occur in the *Tagetes erecta* extract; and oleic, linoleic and linolenic acids are found in the *Capsicum annum* extracts.

By increasing the temperature to 90 to 110° C. under agitation and under an inert atmosphere, the carotenoids' derivatives crystals are melted down in the lipid non-polar matrix producing a homogeneous phase. Although the melting points of pure carotenoids crystals are high, it was observed that the original composition of the matrix and the incorporation of moisture, vegetable oil, additional fatty acids and emulsifiers, as well as a suitable control of the pH media during the melting process, they interact with the carotenoids crystals provoking in situ a sensible decrease of the melting point of the oxycarotenoids derivatives, producing a dispersion of non-crystalline nanoparticles of carotenoids in micellar form with average particle sizes of 2-5 nanometers. The present process generates oxycarotenoid derivatives that interact with the components of the matrix and at the given conditions of temperature, time and agitation, produce carotenoids compounds in a non-crystalline state that upon their incorporation in micelles notably improve their absorption and bioavailability.

The micelles obtained can be diluted with more lipid material. Such lipid material may comprise one or more members selected from the group consisting of vegetable oil, mineral oil, medium chain tryglicerides (MCT) oil (i.e. a triglyceride oil in which the carbohydrate chain has about 8-12 carbon atoms), oily fatty acids, isopropyl myristate, oily fatty alcohols, esters of sorbitol and fatty acids, oily sucrose esters or mixtures thereof. Examples of phospholipids which may be used in the emulsions of the invention are soy lecithins, lecithins; Epikuron 120™ which is a mixture of about 70% phosphatidylcholine and 12% phosphatidylethanolamine and about 15% other phospholipids; Ovothin 160™ or Ovothin 200™. Phosphatidylcholine, 18% phosphatidylethanolamine and 12% other phospholipids; a purified phospholipid mixture, e.g. such which is obtained from egg yolk; Lipoid E-80™ (Lipoid AG, Ludwigshafen); fatty acids as myristic, palmitic, stearic as naturally occur in the *Tagetes erecta* extract; and oleic, linoleic and linolenic acids emulsifiers like Polyoxyethylene sorbitan particularly polysorbate 20-85 such as polysorbate 20, polysorbate 40 polysorbate 60, polysorbate 65, polysorbate 70, polysorbate 80 (Tween 80™), polysorbate 81, polysorbate 85, polyoxyethylene (8) stearate and polyoxyethylene (40), etc. in order to elaborate different preparations or formulations.

An impure solid compound melts at a lower temperature and over a wider range. Thus a solid's compound's melting point may be lowered (depressed) by the addition of a soluble material to the solution.

The melting points (mp) of pure carotenoids, as well as the melting points of some of their derivatives are as follows (The Merck Index, Twelfth Edition, 1996):

Lutein mp . . . 190° C.
Lutein Diacetate mp . . . 170° C.
Lutein Dipropionate mp . . . 138° C.
Lutein Dipalmitate mp . . . 92° C.
Zeaxanthin mp . . . 215° C.
Zeaxanthin Diacetate mp . . . 155° C.
Zeaxanthin Dipropionate mp . . . 142° C.
Zeaxanthin Dipalmitate mp . . . 97° C.
Astaxanthin mp . . . 216° C.
Astaxanthin Diacetate mp . . . 205° C.
Capsanthin mp . . . 182° C.
Capsanthin Diacetate mp . . . 150° C.
Capsanthin Dipalmitate mp . . . 95° C.
Crptoxanthin mp . . . 159° C.
Cryptoxanthin Monoacetate mp . . . 117° C.

It can be observed that the melting points of the pure carotenoids are higher when compared to the melting points of their corresponding derivatives. Therefore in the process to obtain carotenoids derivatives from pure carotenoids, the melting point of oxycarotenoids is reduced from 50 to 116° C. with respect to the melting point of the pure carotenoid, when the diacetate derivatives are incorporated in the process; and the melting point of oxycarotenoids is reduced from 30 to 50° C. with respect to the melting point of the pure carotenoid, when propionate derivatives are incorporated in the process. As the molecular weight of the carotenoid derivative is larger, then the melting point of such derivative is further reduced, as compared to the melting point of the pure carotenoid. Substances such as Tween 80 and/or lecithin or its different compounds, that can be considered as "impurities" (not contaminants) may provoke a sensible reduction of the pure carotenoids melting points. It is important to note that when the carotenoids' derivatives are melted down at such low temperatures, no degradation compounds are obtained in the process.

The obtained micelles can be easily dispersed in water, forming stable microemulsions or nanoemulsions, composed of an internal homogeneous lipophilic phase of carotenoids derivatives that do not contain any crystals, and an external hydrophylic phase formed by lipids and emulsifiers. It is a true oxycarotenoid derivatives solute contained in the micelles. Due to its soft nature such lipid carotenoid derivatives can be easily micronized by means of a homogenizing machine into a microemulsion or a nanoemulsion. Crystalline structures per se are hard to break by mechanical means and therefore are very difficult to be worked into microemulsions and almost impossible to produce nanoemulsions in a non polar media.

Surprisingly when the lipid oxycarotenoid derivatives microemulsions are incorporated in the feed of laying hens or broilers, the pigmentation efficiency is noticeably improved as compared to the pigmentation obtained by premixes or water dispersions that contain the oxycarotenoids in crystalline form.

It is a novelty also to obtain an improved absorption by humans of the oxycarotenoids derivatives as micromicelles in a lipid matrix of free fatty acids, phospholipids, sterols, waxes and different kinds of vegetable or fish oils and emulsifiers' when compared to the absorption of free carotenoids crystals dispersed in oil, regardless of the size of the crystals.

EXAMPLES

The following examples illustrate the improved absorption and bioavailability of the microemulsions and nanoemulsions obtained from the lipid carotenoid derivatives dispersion. These examples are presented for illustrative purposes only and for a better understanding of the invention. However, they are not intended to limit the scope of the present invention.

Example 1

The oxycarotenoids derivatives described in the process of the present invention are prepared according to the following process.

To five (5) kgs of aqueous saponified marigold oleoresin with a pH of 13, 30% diluted acetic acid was added with stirring until a pH of 7.0 was obtained. A separation of phases was observed and the aqueous phase was discarded. The organic phase was rinsed several times with 10 kg of lukewarm water to remove traces of acid and polar compounds. The water was discarded and the temperature was raised to 90° C. and a vacuum of 3 mm Hg was applied under agitation. Once all the moisture was removed from the mass, a quantity of acetic anhydride was added slowly, according to the process described in U.S. Pat. No. 5,959,138, the disclosure of which is incorporated herein by reference.

After the oxycarotenoids diacetate was formed, the lipid matrix was incorporated in a suitable reactor under agitation, 1 kg of fish oil, fatty acid and an emulsifier mixture were added. The vessel was maintained under a nitrogen atmosphere and the temperature rose to 60-70° C. 500 grams of Tween 80 was added and agitated for a period of 120 minutes.

Thereafter, 500 grams of lecithin was added and the mix was stirred for a period of 60 minutes.

The temperature of the reactor was increased to 100° C. until all of the lutein diacetate crystals disappeared, as was observed under a 100× microscope objective.

The mass was immediately cooled down to room temperature and 2 kgs of water were added under agitation to obtain a colloidal suspension. The above procedure was carried out in a closed vessel in the absence of light and under an atmosphere of nitrogen. This procedure aids in the dissolution of crystals and avoids the recrystallization of oxycarotenoids derivatives contained in the original matrix at room temperature. The colloid solution was ready to be dispersed in solid carriers or emulsified in water to the desired concentration.

Example 2

The oxycarotenoids derivatives described in the process of the present invention are prepared according to the following process.

To one (1) kg of aqueous saponified red pepper oleoresin at a pH of 13, a 20% aqueous phosphoric acid solution was added until a pH of 7.0 was reached with stirring. A two phase separation was obtained, and the water phase was discarded. The organic phase was rinsed twice with two portions of 10 kgs of lukewarm water to remove traces of acid and salts. The organic phase in the closed vessel was subjected to a vacuum of 3 mm Hg until all the moisture had been removed. The capsanthin and capsorubin were then converted into diacetates according to the process described in U.S. Pat. No. 5,959,138.

After the oxycarotenoids diacetates has been formed, the lipid matrix was incorporated in a suitable reactor under agitation. The lipid matrix was 500 grams of oleic acid.

The vessel was kept under a nitrogen atmosphere and the temperature was allowed to rise to 60-70° C.

100 grams of a surfactant, polysorbate 60, was added and agitated for a period of 120 minutes.

Thereafter, 200 gr of lecithin was added and the mix was stirred for a period of 60 minutes.

The temperature of the reactor was increased to 95° C. until all of the carotenoids' diacetate crystals disappeared, as was observed under a 100× microscope objective.

The mass was immediately cooled down to room temperature and 2 kgs of water was added under agitation to obtain a colloidal suspension. The above procedure was carried out in a closed vessel in the absence of light and under an atmosphere of nitrogen. This procedure aids in the dissolution of crystals and avoids the oxycarotenoids derivatives contained in the original matrix from recrystallizing at room temperature. The colloid solution is ready to be dispersed in solid carriers or emulsified in water to the desired concentration.

Example 3

The oxycarotenoids derivatives described in the process of the present invention are prepared by the following process.

100 grams of purified free lutein concentrate (85% by weight, AOAC) was blended with 150 grams of food grade oleic acid and 5 grams of α-tocopherol, and the mass was agitated under vacuum for 120 minutes at 90° C. to remove any traces of moisture. A quantity of acetic anhydride was added, according to the process described in U.S. Pat. No. 5,959,138, the disclosure of which is incorporated herein by reference, until all of the lutein was converted into the diacetate.

The mass was rinsed several times with lukewarm water several times to remove any acid traces and salts.

The vessel was kept under a nitrogen atmosphere and the temperature rose risen to 60-70° C.

20 gr of Tween 80 was added and agitated for a period of 120 minutes.

Afterwards, 40 gr of lecithin was added and the mix was stirred for a period of 60 minutes.

The temperature was raised to 100° C. under an atmosphere of nitrogen for a period of 180 minutes until no carotenoid crystals were observed under a 100× microscope objective.

Once the lutein diacetate crystals melted, the mass was cooled below 40° C. and 50 grams of water were added and a colloid suspension was obtained in a high speed agitator. The colloidal suspension can be dispersed in solid carriers, vegetable oils or diluted in water.

Example 4

Two identical groups (Group A and Group B) of three weeks old broilers were placed in suitable pens, each containing 50 chickens. They were fed identical feeds (ad-libitum) containing different pigmenting concentrates. The Group A broilers were feed contained 80 ppm of a blend of micellar lutein diacetate and micellar zeaxanthin diacetate prepared according to example 1. The feed for the Group B broilers contained 90 ppm of a standard lutein pigment (saponified and dispersed in water) plus 3 grams of cantaxanthin.

After four weeks the broilers were slaughtered, processed and refrigerated. The average deposition of pigment in the broilers shank (palmar tissue) was almost identical: 14.9 ppm of total xanthophylls for Group A; and 15.0 ppm of total xanthophylls for Group B.

A Minolta Chromameter was used to determine the pigment reading in the breast skin of each refrigerated broiler. The average readings obtained for each group are as follows:

| Group | Yellowness (b*) | Redness (a*) | Luminosity |
|---|---|---|---|
| A | 27.12 | −1.19 | 76.12 |
| B | 26.21 | 0.90 | 74.09 |

The above data demonstrate that the average person cannot distinguish by the naked eye among the pigmentation of the two groups. However, such information reveals that broilers from Group A, whose feed contained only 80 ppm of micellar lutein diacetate and micellar zeaxanthin diacetate, absorbed much more efficiently the pigment than those from Group B whose feed contained 90 ppm of standard lutein pigment water dispersion plus 3 ppm of red cantaxanthin.

Example 5

Ten (10) healthy non smoking students (ranging in age from 22-27 years), were subjected to the following two treatments:

(A) Four (4) weeks of ingesting one gelatin capsule at their noonday meal, containing 20 mg of crystalline lutein dispersed in soybean oil and after a 12 hours fast (overnight) blood samples were taken early the next morning for plasma analysis.

(B) After a two (2) week interval washout period, the same group of subjects were given, during a period of four (4) weeks, a gelatin capsule containing a micellar dispersion of lutein diacetate (prepared as described in example 3) in soybean oil. Each capsule contained 24.2 mg of lutein diacetate and was ingested at lunch time. After a twelve (12) hour fast, blood samples were collected in the early morning of the next day for plasma analysis.

The results obtained were as follows:

TABLE 1

One gel capsule per day containing 20 mg lutein in soybean oil
Analysis of blood serum in nmol/dL

| Subject | 7 days | 14 days | 21 days | 28 days |
|---|---|---|---|---|
| A | 38.1 | 38.7 | 39.2 | 39.8 |
| B | 23.4 | 24.8 | 26.4 | 27.3 |
| C | 17.5 | 20.5 | 23.8 | 25.1 |
| D | 21.2 | 23.5 | 25.2 | 29.1 |
| E | 20.6 | 21.5 | 22.1 | 22.4 |
| F | 35.7 | 41.0 | 46.0 | 49.7 |
| G | 42.2 | 44.7 | 46.6 | 47.0 |
| H | 15.8 | 16.4 | 17.3 | 19.3 |
| I | 38.1 | 38.9 | 40.1 | 39.2 |
| J | 24.7 | 25.6 | 26.6 | 27.7 |
| Average | 27.7 | 29.6 | 31.3 | 32.6 |
| Std. Dev. | 9.8 | 10.1 | 10.6 | 10.6 |
| Var. Coef. | 0.4 | 0.3 | 0.3 | 0.3 |
| Max | 42.2 | 44.7 | 46.6 | 49.7 |
| Min | 15.8 | 16.4 | 17.3 | 19.3 |

TABLE 2 one gel capsule per day containing 24.2 mg of lutein diacetate in soybean oil
Analysis of blood serum in nmols/dL

| Subject | 7 days | 14 days | 21 days | 28 days |
|---|---|---|---|---|
| A | 76.3 | 88.3 | 99.3 | 118.7 |
| B | 46.3 | 51.6 | 57.1 | 68.1 |
| C | 31.5 | 39.3 | 49.3 | 65.2 |
| D | 39.4 | 51.2 | 63.0 | 84.1 |
| E | 40.2 | 46.2 | 52.5 | 62.6 |
| F | 66.7 | 87.1 | 106.8 | 146.8 |
| G | 82.3 | 98.9 | 113.0 | 134.0 |
| H | 23.6 | 29.4 | 35.6 | 48.2 |
| I | 71.3 | 81.8 | 94.6 | 115.8 |
| J | 46.6 | 51.9 | 60.3 | 74.1 |
| Average | 52.4 | 62.6 | 73.1 | 91.8 |
| Std. Dev. | 20.2 | 24.1 | 27.5 | 34.2 |
| Var. Coef. | 0.4 | 0.4 | 0.4 | 0.4 |
| Max | 82.3 | 98.9 | 113.0 | 146.8 |
| Min | 23.6 | 29.4 | 35.6 | 48.2 |

The improvement in the absorption and bioavailability can be determined by the ratio of the average absorption of the lutein diacetate (Table 2), divided by the average absorption of the free lutein (Table 1): 91.8/32.6=2.81 times.

We claim:

1. A process for obtaining stable microemulsions that are composed of a solubilizate of derivatives of oxycarotenoids of short chain organic acids, selected from the group consisting of diacetates and dipropionates of lutein, 3'epilutein, zeaxanthin, iso zeaxanthin, meso zeaxanthin, capsanthin, capsorubin, astaxanthin, and cryptoxanthin monoacetate and monopropionate, which are melted down from the naturally occurring original lipid vegetable matrix in the presence of lipids, phospholipids, fatty acids, emulsifiers and moisture, which process comprises the steps of:
   a) adding diacetate and dipropionate derivatives of said oxycarotenoids with sterols, fatty acids, lipids, phospholipids, emulsifiers, or mixtures thereof, derived from a vegetable matrix in a reactor;
   b) raising the temperature of the reactor to about 60 to about 70° C.;
   c) adding a surfactant to obtain a mixture of derivatives of oxycarotenoids and a surfactant;
   d) stirring the mixture obtained in step c) for a period of time sufficient to homogenize the mixture;
   e) adding to the mixture obtained in step d) from about 5% to about 50%, by weight, of a phospholipid;
   f) stirring the mixture obtained in step e) for a period of time sufficient to homogenize the mix;

g) adding to the mixture obtained in step f) about 1% to about 40%, by weight, of water; and h) raising the temperature of the mixture obtained in step g) to about 90 to about 110° C. while maintaining the pH at from about 5.5 to about 8.5 and refluxing the mixture for a period of time sufficient to melt the crystals of the oxycarotenoids derivatives in the non polar lipid matrix whereby microemulsions of the oxycarotenoids derivatives are formed.

2. The process as claimed in claim 1, wherein the surfactant comprises from about 5 to 50%, by weight, of a surfactant selected from the group consisting of polyoxyethylene sorbitan, polyoxyethylene stearate, polyoxyethylene oleate polyoxyethylene laureates, sorbitan esters, poloxamers and tyloxapol, and polyoxy-ethylene fatty acid esters.

3. The process as claimed in claim 1, wherein the phospholipid is selected from the group consisting of a zwitterionic surfactant; a surfactant consisting of about 70% phosphatidylcholine and 12% of a surfactant consisting of phosphatidylcholine, 18% phosphatidylethanolamine and 12% other phospholipids) or a purified egg yolk, or a surfactant consisting of about 50% phosphatidylcholine, 5% phosphatidylethanolamine, 3.6% non-polar lipids and about 2% sphingomyeline.

4. The process as claimed in claim 1, wherein in step g) the soluble material comprises fatty acids selected from the group consisting of myristic acid, palmitic acid, stearic acid, oleic acid, linoleic acid, linolenic acid, sterols, methyl sterols, vegetable $C_{40}$, $C_{42}$, and $C_{46}$ waxes, tocopherols, tocotrienols, phospholipids, and mixtures thereof.

5. The process as claimed in claim 1, wherein in step h) the pH is maintained at about 6.5 to about 7.0.

6. The process as claimed in claim 1, wherein step h) is carried out in a vacuum.

7. The process as claimed in claim 1, wherein the microemulsions of derivatives of oxycarotenoids are dispersed in an aqueous or lipid media suitable for incorporation in human supplements or foods, or feeds for pets, poultry or aquatic animals.

8. The process as claimed in claim 1, wherein the microemulsions of derivatives of oxycarotenoids are dispersed in an aqueous or lipid media at a temperature of between about 40 to about 70° C.

9. The process as claimed in claim 1, wherein the microemulsions of derivatives of oxycarotenoids are dispersed in an aqueous or lipid media to improve the absorption and bioavailability of xanthophylls diacetates and dipropionates obtained from lutein, zeaxanthin, capsanthin and capsorubin for use in the pigmentation of the skin of broilers and egg yolks.

10. The process as claimed in claim 1, wherein the microemulsions of derivatives of oxycarotenoids are dispersed in an aqueous or lipid media to improve the absorption and bioavailability of the carotenoids derivatives obtained from lutein, zeaxanthin, capsanthin, capsorubin, and astaxanthin when incorporated in the feed of marine organisms.

11. The process as claimed in claim 1, wherein the microemulsions of oxycarotenoids derivatives are dispersed in lipids or water containing carotenoids derivatives obtained from lutein, 3'epilutein, zeaxanthin, isozeaxanthin, mesozeaxanthin, capsanthin, capsorubin, astaxanthin and cryptoxanthin, which can be administered to humans as a supplement to prevent and protect cells and tissues from the damaging effect of free radicals and singlet oxygen, as well as to prevent the risk of cancers and stroke.

12. The process as claimed in claim 1, wherein the microemulsions of diacetates and dipropionates of oxycarotenoids of lutein, 3'epilutein, zeaxanthin, isozeaxanthin are dispersed in fish oil with a high content of omega 3 fatty acids which aids in reducing the risk of macular degeneration and the formation of cataracts in humans when ingested.

13. The process as claimed in claim 1, wherein the microemulsions containing oxycarotenoids derivatives of diacetates or dipropionates of lutein, 3'epilutein, zeaxanthin, Isozeaxanthin, are dispersed in fish oil with a high content of omega 3 fatty acids, whereby the cardiovascular health of humans is improved when ingested.

14. The process as claimed in claim 1, wherein the melting point of the oxycarotenoids are reduced by about 50 to about 116° C. with respect to the melting point of the pure carotenoid when the diacetate derivatives are incorporated in the process and the melting point of the oxycarotenoids is reduced by 30 to 50° C. with respect to the melting point of the pure carotenoid when propionate derivatives are incorporated in the process.

15. The process as claimed in claim 1, wherein the microemulsions obtained can be reduced in size to obtain nanoemulsions by the use of intense high speed and high shear mechanical agitators, or by emulsifying machines operating at pressures of the order of about 3,000 to about 4,000 psi.

16. The process as claimed in claim 1, wherein the microemulsions of oxycarotenoids derivatives obtained from lutein, 3'epilutein, zeaxanthin, iso zeaxanthin, meso zeaxanthin, capsanthin, capsorubin, and astaxanthin are encapsulated by maltodextrins, sugars, animal, vegetable or fish gelatins, to prepare beadlets for supplementing human nutrition.

* * * * *